United States Patent
Wright et al.

(10) Patent No.: US 6,589,957 B2
(45) Date of Patent: *Jul. 8, 2003

(54) COMPOUNDS AND METHODS OF USE FOR TREATMENT OF NEUROGENIC INFLAMMATION

(75) Inventors: Amy E. Wright, Fort Pierce, FL (US); Shirley A. Pomponi, Fort Pierce, FL (US); Robert S. Jacobs, Santa Barbara, FL (US)

(73) Assignees: Harbor Branch Oceanographic Institution, Inc., Fort Pierce, FL (US); Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/944,881

(22) Filed: Aug. 31, 2001

(65) Prior Publication Data

US 2002/0016327 A1 Feb. 7, 2002

Related U.S. Application Data

(63) Continuation of application No. 09/253,118, filed on Feb. 19, 1999, now Pat. No. 6,291,501.
(60) Provisional application No. 60/091,990, filed on Jul. 8, 1998, and provisional application No. 60/075,476, filed on Feb. 20, 1998.

(51) Int. Cl.$^7$ ................... C07D 471/04; A61K 31/496

(52) U.S. Cl. ................... 514/255.05; 594/405

(58) Field of Search ....................... 544/405; 514/255.05

(56) References Cited

U.S. PATENT DOCUMENTS

| | | | |
|---|---|---|---|
| 4,866,084 A | 9/1989 | Gunasekera et al. | |
| 4,895,844 A | 1/1990 | Komoto et al. | |
| 5,290,777 A | 3/1994 | McConnell et al. | |
| 5,464,835 A | 11/1995 | McConnell et al. | |
| 5,496,950 A | 3/1996 | McConnell et al. | |

FOREIGN PATENT DOCUMENTS

| | | |
|---|---|---|
| WO | 9818466 | 5/1987 |
| WO | 9404494 | 3/1994 |
| WO | 9419343 | 9/1994 |
| WO | 9532966 | 12/1995 |
| WO | 9533744 | 12/1995 |

OTHER PUBLICATIONS

Bifulco, G., I. Bruno, L. Minale, R. Riccio, A. Calignano, C. Debitus (1994) *J. Nat. Prod.* 57:1294.
Bifulco, G., I. Bruno, R. Riccio, J. Lavayre, G. Bourdy (1995) *J. Nat. Prod.* 58:1254.
Scheuer, P.J. ed. (1978–1983) In: *Marine Natural Products, chemical and Biological Perspectives* Academic Press, New York.
Faulkner, D. (1995) *Natural Products Report* 12:223–269.
Faulkner, D. (1994) *Natural Products Report* 11:355–394.
Faulkner, D. (1993) *Natural Products Report* 10:497–539.
Faulkner, D. (1992) *Natural Product Reports* 9:323–364.
Faulkner, D. (1991) *Natural Product Reports* 8:97–147.
Faulkner, D. (1990) *Natural Products Report* 7:269–309.
Faulkner, D. (1988) *Natural Products Report* 5:613–663.
Faulkner, D.J. (1987) Natural Products Report 4(5)539–576.
Faulkner, D. J. (1986) *Naurals Products Report* 3:1–33.
Faulkner, D. (1984) *Natural Products Report* 1:551–598.
Jiminez, C., E. Quinoa, P. Crews (1991) *Tetrahedron Lett.* 32:1843.
Jimenez, C., E. Quinoa, M. Adamczesky, L.M. Hunter, P. Crews (1991) *J. Org. Chem.*56:3403.
Kobaryashi, H., T. Ohta, S. Nozoe (1990) *Tetrahedron Lett.* 46:7699.
Moquin, C., Guyot (1984) *Tetrahedron Lett.* 25(44):5047–5048.
Norton, R. S.,R.J. Wells (1982) *J. Am. Chem. Soc.* 104:3628–3635.
Roll, D.M., C. M. Iireland, H.S.M. Lu, J. Clardy (1988) *J. Org. Chem.* 53:3276.
Mancini, Ines et al. (1996) "From inactive nortopsentin D, a novel bis(indole) alkaloid isolated from the axinellid sponge Dragmacidon sp. from deep waters south of New Coledonia, to a strongly cytotoxic derivative" *Helv. Chim. Acta.* 79(8):2075–2082.
Wylie, B. et al. (1997) "Marine Natural products as phospholipase A2 inhibitors" *Basic and Clinical Aspects in Inflammatory Diseases* 146–152.

*Primary Examiner*—Robert Gerstl
(74) *Attorney, Agent, or Firm*—Saliwanchik, Lloyd & Saliwanchik

(57) ABSTRACT

The subject invention pertains to compounds which are useful as anti-inflammatory agents and to compositions containing such compounds as active ingredients. The novel uses of the compounds relate to the anti-neurogenic inflammatory properties of the disclosed bis-heterocyclic compounds. Specifically exemplified herein are dragmacidin f, topsentin d, and topsentin e, and their salts, analogs, and derivatives.

25 Claims, No Drawings

COMPOUNDS AND METHODS OF USE FOR TREATMENT OF NEUROGENIC INFLAMMATION

CROSS-REFERENCE TO A RELATED APPLICATION

This application is a continuation of application Ser. No. 09/253,118, filed Feb. 19, 1999 now U.S. Pat. No. 6,291,501; which claims priority to provisional patent application Serial No. 60/091,990, filed Jul. 8, 1998; and Serial No. 60/075,476, filed Feb. 20, 1998.

DESCRIPTION

The subject invention was made with government support under a research project supported by NOAA Grant No. NA36RG0537. The government has certain rights in this invention.

FIELD OF THE INVENTION

The subject invention pertains to compounds which are useful as anti-inflammatory agents and to compositions containing such compounds as active ingredients. More particularly, the invention concerns novel biologically active bis-heterocyclic compounds, e.g. bis-indoles, novel uses of the compounds, pharmaceutical compositions containing these compounds, and methods of producing the compounds. The novel uses of the compounds relate to the anti-neurogenic inflammatory properties of the disclosed bis-heterocyclic compounds. Specifically exemplified herein are dragmacidin f, topsentin d and topsentin e, and their salts, analogs and derivatives.

BACKGROUND OF THE INVENTION

The prevention and control of inflammation is often of great importance for the treatment of humans and animals. Much research has been devoted to development of compounds having anti-inflammatory properties. Certain methods and chemical compositions have been developed which aid in inhibiting or controlling inflammation, but additional anti-inflammatory methods and compositions are needed.

It has been found that some natural products and organisms are potential sources for chemical molecules having useful biological activity of great diversity. Marine sponges have proved to be such a source, and a number of publications have issued disclosing organic compounds derived from marine sponges. Such publications include Scheuer, P. J. Ed. (1978–1983) *Marine Natural Products, Chemical and Biological Perspectives,* Academic Press, New York; Faulkner, D. (1995) *J. Nat. Prod. Rep.* 12:223–269; (1994) 11:355–394; (1993) 10:497–539; (1992) 9:323–364; (1991) 8:97–147; (1990) 7:269–309; (1988) 5:613–663; (1987) 4:539–576; (1986) 3:1–33; (1984) 1:551–598.

Indole compounds of marine origin have also been described in Moquin, C., M. Guyot (1984) Tetrahedron Letters 25 (44):5047–5048; Norton, R. S., R. J. Wells (1982) *J. Am. Chem. Soc.* 104: 3628–3635; Roll, D. M., C. M. Iireland, H. S. M. Lu, J. Clardy (1988) *J. Org. Chem,* 53:3276; Kobayashi, H., T. Ohta, S. Nozoe (1990) *Tetrahedron* 46:7699; Jiminez, C., E. Quinoa, P. Crews, (1991) *Tetrahedron Lett.* 32:1843; Jiminez, C., E. QUinoa, M. Adamczeski, L. M. Hunter, P. Crews (1991) *J. Org. Chem.* 56:3403; Bifulco, G., I. Bruno, L. Minale, R. Riccio, A. Calignano, C. Debitus (1994) *J. Nat. Prod.* 57:1294; and Bifulco, G., I. Bruno, R. Riccio, J. Lavayre, G. Bourdy (1995) *J. Nat. Prod.* 58:1254.

Utilizing sponges as a source material and supplemented by synthetic production methods, new classes of biologically active compounds and new pharmaceutical compositions useful as antitumor and antiviral agents have been provided to the art. For example, bis-heterocyclic compounds such as bis-indoles have been previously described as having antimicrobial, antitumor or antiviral activity. Specifically, the bis-indole compounds known as topsentins are disclosed in U.S. Pat. No. 4,866,084. Dragmacidin and its related compounds isolated from the marine sponge of the *Dragmacidon* sp. are disclosed in U.S. Pat. No. 4,895,844. These patents are herein incorporated by reference. These compounds as well as the homocarbonyl topsentins and hamacanthins have also been described as having inhibitory activity against cellular inflammatory responses. See U.S. Pat. Nos. 5,290,777 and 5,464,835, which are also hereby incorporated by reference. The present invention provides additional related compounds which have improved water solubility characteristics and which have a novel utility as anti-neurogenic inflammatory compositions.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The objects of the present invention are accomplished by the provision of novel anti-inflammatory bis-heterocyclic compounds that have a general structure according to the formula:

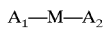

wherein each of $A_1$ and $A_2$ is a heterocycle; and M is a core moiety linking the heterocycles, $A_1$ and $A_2$. In a specific embodiment, the compound comprises an indole as the $A_1$ and $A_2$ moieties. Thus, the compound can be a bis-indole. Other compounds of the subject invention can comprise heterocycles such as pyridyl or purine as the $A_1$ and $A_2$ moieties. The core moiety M can be a linear or cyclic group comprising at least three atoms.

Specifically exemplified herein are the novel compounds which have been designated as dragmacidin f, topsentin d, and topsentin e. Advantageously, these compounds have been found to possess anti-neurogenic inflammation activity.

As described herein, the invention also comprises pharmaceutical compositions, e.g. anti-neurogenic inflammatory compositions, containing as an active ingredient an effective amount, of one or more compounds according to the formula expressed above and a non-toxic, pharmaceutically acceptable carrier or diluent. The pharmaceutical compositions of the subject invention can further comprise other active compounds. Such other active compounds include, but are not limited to, anti-inflammatory compounds for example, steroidal compounds, including hydrocortisone and the like; or non-steroidal anti-inflammatories, including acetylsalicylic acid (aspirin), ibuprofen, acetaminophen, indomethacin, and the like. The second active ingredient can include antiviral, antibacterial, antifungal or other antimicrobial compounds or antitumor compounds as well.

As described herein, the invention further comprises processes for the production of compounds and compositions of the invention and novel methods of use thereof, e.g.

methods of inhibiting a neurogenic inflammatory response in a human or animal.

In accordance with the invention, methods for inhibiting inflammation comprise administering to a human or animal in need of such treatment an effective amount of the pharmaceutical composition

DETAILED DESCRIPTION OF THE INVENTION

The subject invention pertains to novel uses as anti-inflammatory agents of bis-heterocyclic compounds and compositions comprising the bis-heterocyclic compounds. Surprisingly, the bis-heterocycle compounds of the subject invention can be highly effective in inhibiting neurogenic inflammation.

A specific embodiment of the subject invention is a bis-indole compound, wherein one of the indole rings has been reduced and an internal cyclization has taken place between a 2-aminoimidazolyl-ethylamine side chain and one of the indole rings as shown in structure (I) below:

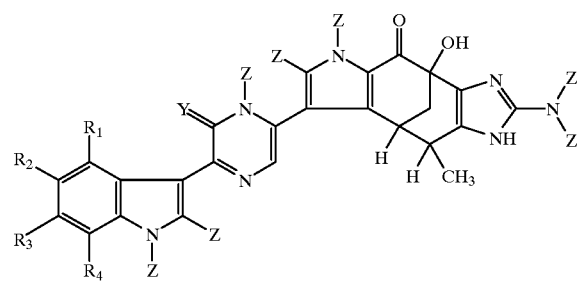

(I)

$R_{1-4}$ are the same or different selected from —H, —OH, halogen, —R, —OR, —OCOR, —OA, or NZZ (wherein the Zs can be the same or different);

Y is the single group =O, or the single group =NZ, or two groups, same or different, selected from —H, —OH, —OR, —OCOR, NZZ (wherein the Zs can be the same or different);

Z is independently selected from —H, —R, —OH, or —COR;

R is C1–C8 alkyl or C1–C8 alkoxyl, mesyl, or tosyl; and

A is —R-phenyl.

A particularly preferred embodiment is the compound called dragmacidin f (structure (II), below), and salts thereof. In this compound, $R_1=R_2=R_4=Z=H$; $R_3=Br$; Y is the single group =O.

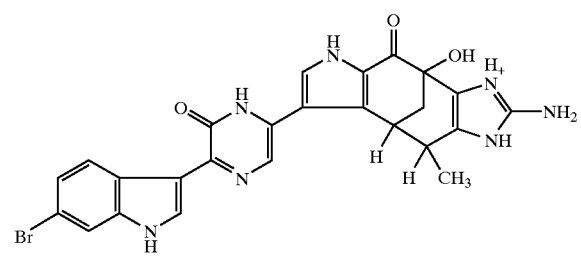

(II)

A specific embodiment of the invention includes compounds in which alkylation of the imidazole ring of the topsentins has occurred as shown in structure (III) below:

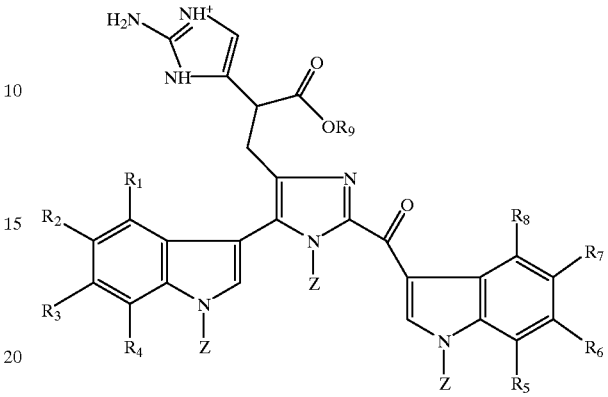

(III)

wherein $R_{1-8}$ are the same or different selected from —H, —OH, halogen, —R, —OR, —OCOR, —OA, or NZZ (wherein the Zs can be the same or different);

R is $C_{1-8}$ alkyl or aryl;

Z is independently selected from —H, —R, —OH, or —COR;

R is $C_{1-8}$ alkyl or $C_{1-8}$ alkoxyl, mesyl, or tosyl; and

A is —R-phenyl.

A particularly preferred embodiment is the compound in which $R_1=R_2=R_4=Z=H$ and $R_3=Br$ and $R_6=OH$, and salts thereof, as shown below in topsentin d (IV):

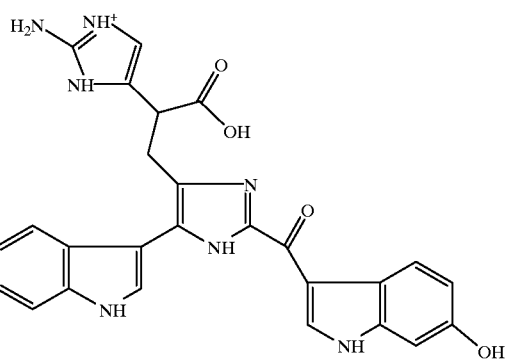

(IV)

A specific embodiment of the invention includes compounds in which alkylation of the imidazole ring of the topsentins has occurred as shown in structure (V) below:

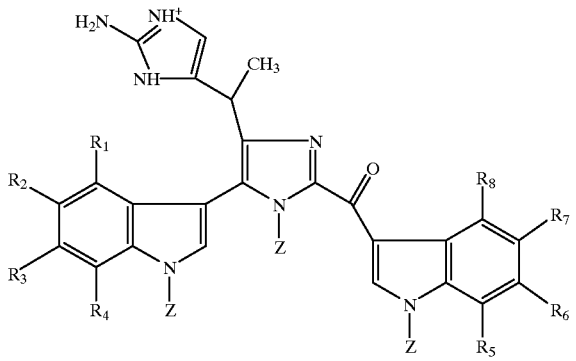

(V)

wherein $R_{1-8}$ are the same or different selected from —H, —OH, halogen, —R, —OR, —OCOR, —OA, or NZZ (wherein the Zs can be the same or different);

R is $C_{1-8}$ alkyl or aryl;

Z is independently selected from —H, —R, —OH, or —COR;

R is $C_{1-8}$ alkyl or $C_{1-8}$ alkoxyl, mesyl, or tosyl; and

A is —R-phenyl.

A particularly preferred embodiment is the compound in which $R_1=R_2=R_4=Z=H$ and $R_3=Br$ and $R_6=OH$, and salts thereof, as shown below in topsentin e (VI):

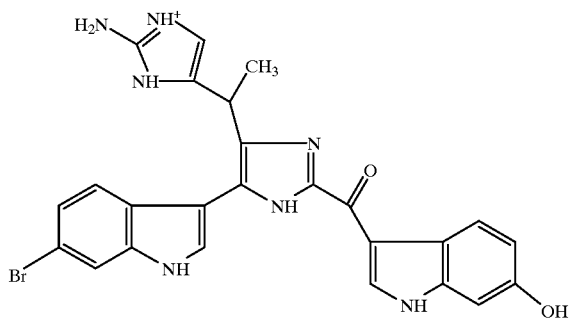

(VI)

Skilled chemists having the benefit of the instant disclosure, can readily use procedures to prepare the subject compounds. In carrying out such operations, suitable filtration, chromatographic and other purification techniques can be used. These techniques could include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents such as heptane, ethyl acetate, methylene chloride, methanol, isopropanol, acetonitrile water, trifluoroacetic acid (TFA) and various combinations thereof.

One method of preparation of the compounds used according to the subject invention involves extraction from marine sponges of the genus Spongosorites (Phylum Porifera, Class Demospongiae, Order Halichondrida, Family Halichondriidae). Certain of the samples used in connection with this invention have been assigned to the species Spongosorites ruetzleri (HBOM Catalog Numbers 003:00112, 003:00113, 003:00114, 003:00115, 003:00116, 003:00117, 003:00118, 003:00119, 003:00120, 003:00927); other specimens represent new species of Spongosorites (HBOM Catalog Numbers 003:00549 and 003:00696). For descriptions of these samples and other Spongosorites species, refer to Diaz., M. C., Pomponi, S. A. and Van Soest, R. W. M. (1993) "A systematic revision of the central West Atlantic Halichondrida (Demospongiae, Porifera), Part III: Description of valid species," Scientia Marina, 57(4): 283–306. All taxonomic voucher samples cited herein with HBOM Catalog Numbers are deposited in the Harbor Branch Oceanographic Museum, Fort Pierce, Fla. All voucher specimens are preserved in 70% ethanol with an expected shelf life of at least 30 years and are accessible to those skilled in the art for taxonomic identification purposes.

A novel use for the described compounds and compositions is their administration to an animal or human as an agent in the control of a neurogenic inflammatory response. Anti-inflammatory activity against cellular activation of specific immune cells, e.g., phorbol myristate acetate (PMA)-induced inflammation, has been described for the subject compounds. See U.S. Pat. Nos. 5,290,777 and 5,464,835, which are hereby incorporated by reference. However, it is well recognized that activity of a compound in inhibiting cellular activated inflammation (e.g., PMA-induced edema or inflammation) is not predictive or suggestive of that compound's activity in inhibiting neurogenic inflammation, e.g., capsaicin-induced or resiniferatoxin (RTX)-induced edema or inflammation.

Therefore, the discovery that the subject compounds have inhibitory activity against neurogenic inflammation is unexpected and advantageous. Neurogenic inflammation is evoked by neuropeptides released from primary afferent nerve terminals and by other secondarily released inflammatory mediators. Specifically, neurogenic inflammation can be evoked by neuropeptides, such as substance P(SP), calcitonin gene-related peptide (CGRP), vasoactive intestinal peptide (VIP), and neurokinin A(NKA), released from primary afferent C-fiber nerve terminals and histamine, secondarily released from mast cells (Dray, A., [1992] "Neuro pharmacological mechanisms of capsaicin and related substances" Biochem Pharm 44(4):611–15). For purposes of the subject invention, unless otherwise noted, the terms "inflammation" and "inflammatory response" refer to any and all such neurogenic inflammatory reactions including, but not limited to, immune-related responses and/or allergic reactions to a physical, chemical, or biological stimulus. "Anti-neurogenic inflammatory activity," as used herein, will be understood by those of ordinary skill in the art to mean biological activity inhibiting or controlling a neurogenic inflammatory response.

Anti-inflammatory activity can occur by modes of action which can include, but are not limited to, lipid-mediated inflammatory responses, e.g., (i) suppression of cellular activation of phospholipase A2, either directly (as is known for the anti-inflammatory compound, manoalide) or indirectly (as is known for the anti-inflammatory compound, hydrocortisone); (ii) by inhibiting, or controlling, cyclooxygenation of arachidonic acid, similar to the action of non-steroidal anti-inflammatory drugs; or (iii) by affecting lipooxygenase products of peroxidase reactions to arachidonic acid, or by non-lipid-mediated inflammatory responses, e.g., protease-induced inflammatory responses, and the like. In addition, it is known that capsaicin (CAP), the active constituent found in cayenne pepper, induces an acute neurogenic inflammatory response when applied topically to skin. CAP is a highly selective pain producing substance that selectively stimulates nociceptive and thermal-sensitive nerve endings in tissues by acting on a specific membrane receptor. The mode of action of capsaicin therefore differs significantly from phorbol myristate acetate (PMA)-induced inflammation. By comparison, PMA elicits its pro-inflammatory effects through cellular activation of specific immune cells, such as macrophages and neutrophils. Consequently, the pain response to PMA develops more slowly than the immediate, but transient, pain response to capsaicin.

The compounds and compositions of the subject invention advantageously can block the nociceptive (CAP-induced) inflammatory pathway, thereby providing a method for inhibiting neurogenic inflammation. Accordingly, the compounds can be used in the treatment of inflammation at sites where the primary activating factor is of neurogenic origin, e.g., inflammatory bowel disease or nepehritis. The subject compounds and compositions can be useful in the treatment of chronic pain, migraines, thermal-induced pain, such as sunburn, or other thermal and nociceptive pain, and chronic pain associated with arthritis. Uses can also include other inflammatory conditions that involve a neurogenic pain-producing component, e.g., certain metastic carcinomas or inflammation of the blood vessels.

The compounds of the subject invention can be used to treat a variety of skin conditions including, but not limited to, radiation irritation and burns (including UV and ionizing), chemical burns, rhinitis, thermal burns, reddening of the skin, and chemically indued lesions.

The compounds of the subject invention can also be used to treat allergic response and/or promote wound healing. This can include the use of the compounds in aerosol form for the treatment of acute allergic reactions such as acute asthmatic attack and in the treatment of inflammation of the lung caused by chemical exposure.

The compounds of the subject invention can also be used to treat systemic anaphylactic reactions in animals and man.

The compounds of the subject invention can also be used to treat conjunctivitis and inflammatory gum diseases.

Following are examples which illustrate procedures for practicing the invention. A more complete understanding of the invention can be obtained by reference to the following specific examples of compounds, compositions, and methods of the invention. It will be apparent to those skilled in the art that the examples involve use of materials and reagents that are commercially available from known sources, e.g., chemical supply houses, so no details are given respecting them. These examples should not be construed as limiting. All percentages are by weight and all solvent mixture proportions are by volume unless otherwise noted.

EXAMPLE 1

Preparation of Dragmacidin f (II)

Taxonomic and Collection Data.

A sample of *Spongosorites sp.* (Phylum Porifera, Class Demospongiae, Order Halichondrida, Family Halichondriidae, HBOI no. 22-VIII-90-3-004) was collected by dredge at a depth off 300 feet of Gran Canaria, Canary Islands (Latitude 27 45.75' N, Longitude 15 47.90' W). This specimen of *Spongosorites* is spherical in shape and consolidates sediment. A voucher specimen of the sponge has been deposited at the Harbor Branch Oceanographic Museum, Catalog Number 003:00156.

Isolation of Dragmacidin f (II).

The frozen sponge (35 g) was extracted exhaustively with ethanol by macerating in a Waring blender. The extract was filtered and then concentrated to a dark orange oil by distillation under reduced pressure. The residue was partitioned between ethyl acetate and water. The methanol soluble portion of the water partition was chromatographed under vacuum column chromatographic conditions on an RP-18 stationary phase. The column used had a volume of 360 ml and was 4 cm in height. The column was eluted with a step gradient of acetonitrile-water-trifluoroacetic acid. The methanol soluble materials (797.8 mg) were applied to the column as a slurry adsorbed onto RP-18 packing using water containing 0.1% trifluoroacetic acid (TFA). The column was eluted as follows: fraction 1, 100 mL of water containing 0.1% TFA; fraction 2, 50 mL of water-ACN-TFA (40:10:0.05 v/v/v); fraction 3, 50 mL of water-ACN-TFA (30:20:0.05 v/v/v); fraction 4, 50 mL of water-ACN-TFA (20:30:0.05 v/v/v); fraction 5, 50 mL of water-ACN-TFA (10:40:0.05 v/v/v); fraction 6, 50 mL ACN. Fractions 2–4 were combined (179.6 mg) and chromatographed a second time under vcc conditions. The column (150 ml, 3 cm in height) was eluted as follows: fraction 1, 50 mL of water containing 0.1% TFA; fraction 2, 50 mL of water-ACN-TFA (40:10:0.05 v/v/v); fraction 3, 100 mL of water-ACN-TFA (30:20:0.05 v/v/v); fraction 4, 50 mL of water-ACN-TFA (20:30:0.05 v/v/v); fraction 5, 50 mL of water-ACN-TFA (10:40:0.05 v/v/v); fraction 6, 50 mL ACN. Fraction 3 was further separated by HPLC on a Vydac C-18 protein and peptide column (4.6 mm×25 cm) using water-ACN-TFA (70:30:0.1) as eluent (flow rate=1 ml/min). Pure dragmacidin f, II, eluted after seven column volumes.

Spectral data:

HRFABMS: m/z 546.0821 $C_{25}H_{21}BrN_7O_3$ (calculated–observed=–0.2 mmu).

$^{13}C$ NMR (125 MHZ, DMSO-$d_6$ trace of TFA); 14.89 q; 31.25 d; 34.69 d; 43.52 t; 71.17 s; 111.79 s; 114.35 d; 114.87 s; 115.0 s; 121.24 s; 123.09 d; 123.96 s; 124.29 d; 124.96 s; 126.94 s; 127.12 d; 127.13 d; 130.69 s; 130.69 s; 131.15 d; 137.23 s; 147.78 s; 147.78 s; 158.48 s; 187.05 s.

$^1H$ NMR (500 MHZ, DMSO-$d_6$ trace of TFA): 0.78 d (J=7.0 Hz); 2.29 dd (J=12.1, 2.4 Hz); 2.54 dd (J=12.1, 3.0 Hz); 3.29 m; 4.15 bs; 726 dd (J=8.6, 1.8 Hz); 7.54 bs; 7.54 d (J=2.9 Hz); 7.67 d (J=1.8 Hz); 8.55 d (J=8.6 Hz); 8.73 s; 11.67 s; 12.20 s; 12.39 s; 12.40 s.

EXAMPLE 2

Preparation of Topsentin D (III) and Topsentin E (IV)

Taxonomic and Collection data. A sample of *Spongosorites sp.* (Phylum Porifera, Class Demospongiae, Order Halichondrida, Family Halichondriidae, HBOI No. 21-V-93-3-001 was collected at a depth of 2067 feet using the Johnson-Sea Link Submersible near Long Island, west of Cape Santa Maria, Bahamas (Latitude 23 41.117' N Longitude 75 22.182' W). The sponge is thick encrusting with a yellow-white external color and a yellow internal color. As voucher specimen has been deposited in the Harbor Branch Oceanographic Museum (Catalog Number 003:00936).

Isolation of topsentin $d_r$(III).

The frozen sponge (250 g) was extracted exhaustively with ethanol by macerating in a Waring blender. The extract was filtered and then concentrated to a dark orange oil (15.9 g) by distillation under reduced pressure. The residue was partitioned between n-butanol and water. The butanol partition (4.1 g) was chromatographed under vacuum column chromatographic conditions on an RP-18 stationary phase. The column used had a volume of 360 ml and was 4 cm in height. The column was eluted with a step gradient of acetonitrile-water-trifluoracetic acid. The materials were applied to the column as a slurry adsorbed onto RP-18 packing using water containing 0.1% trifluoroacetic acid (TFA). The column was eluted as follows; fraction 1,100 mLs of water containing 0.1% TFA; fraction 2,100 mLs of water-ACN-TFA (80:20:0.1 v/v/v); fraction 3,100 mLs of water-ACN-TFA (60:40:0.1 v/v/v); Fraction 4,100 mLs of water-ACN-TFA (40:60:0.1 v/v/v); fraction 5,100 mLs of water-ACN-TFA (20:80:0.1 v/v/v); fraction 6, 100 mLs ACN. Fraction 3 was further separated by hplc on a Vydac C-18, protein and peptide column (1 cm x 25 cm) using water-ACN-TFA (76:24:0.1) as eluent (flow rate=3 ml/min) to yield topsentin d (IV) 15.1 mg and topsentin e (VI) 10.4 mg.

Spectral data: Topsentin d (IV):

HRFABMS: 574.149 formula $C_{26}H_{21}N_7O_4Br$.

$^{13}C$ NMR (125 MHZ, $d_6$-DMSO+trace of TFA): 172.48 s, 172.25 s, 155.52 s, 147.68 s, 142.68 s, 138.52 s, 137.77 d, 137.36 s, 131,55 s, 128.1 d, 127.12 s, 126.71 s, 125.75 s, 123.13 d, 122.30 d, 121.37 d, 119.08 s, 115.2 s, 115.05 d, 113.6 d, 110.77 d, 102.27 s, 98.29 d,37.92t, 29.60d.

$^1H$ NMR (500 MHZ, $d_6$-DMSO+trace of TFA): 12.13 s, 12.01 s, 11.74 s (2 H), 8.43 d J=2 Hz, 8.02 d J=9 Hz, 7.68 s (2 H), 7.53 d J=9 Hz, 7.2 dd J=9, 2 Hz, 6.92 d J=2 Hz, 6.79 dd J=9, 2 Hz, 4.55 m, 3.08 m (2 H).

Spectral data: Topsentin e (VI)

HRFABMS: 530.0942 Formula: $C_{25}H20N_7O_2Br$.

$^{13}C$ NMR(125 MHZ, $d_4$-methanol): 172.8 s, 155.1 s, 147.9 s, 144.5 s, 138.6 s, 137.6 s, 136.8 d, 136.8 s 129.9 s, 123.4 d, 126.7 s, 126.6 d, 122.5 d, 120.4 d, 120.0 s, 115.8 d, 114.7 d, 112.6 d, 126.0 s, 114.9 s, 109.5 d, 103.9 s, 97.6 d, 28.7 d, 18.0 q.

$^1H$ NMR (500 MHZ, $d_4$-methanol): 8.55 s, 8.13 d J=11.8 Hz, 7.65 s, 7.51 s, 7.49 dd J=11.8, 2.5 Hz, 7.25 dd J=11.8, 2 Hz, 6.92 d J=2.5, 6.87 bd J=11.8, 6.48 s, 4.30 q J=9.5 Hz, 1.69 d J=9.5 Hz.

EXAMPLE 3

Inhibition of Resiniferatoxin-Induced Inflammation (Edema) of the Mouse Ear

Induction of mouse ear edema can be conducted by known methods (Inoue, 1-f., N. Nagata, Y. Koshffiara [1993]). Compounds to be tested for anti-neurogenic inflammatory activity are topically applied in acetone to the ears of mice in a solution that includes the edema-causing irritant resiniferatoxin (RTX). RTX alone (0.1 µg/ear) or in combination with various dilutions of test compound are applied to both sides of the left ears (5 mice per treatment group) and acetone is applied to all right ears. After a 30-minute incubation, the mice are sacrificed, the ears removed, and bores taken and weighed. Edema is measured by subtracting the weight of the right ear (acetone control) from the weight of the left ear (treated). Results are recorded as % decrease (inhibition) or % increase (potentiation) in edema relative to the control group edema.

Bis-heterocycle compounds of the subject invention, e.g., the bis-indole compounds, show significant anti-inflammatory properties. When screened for the ability to reduce edema in mouse ears caused by application of resiniferatoxin (RTX), a known inflammatory agent, a dose of 50 µg/ear of topsentin d, (IV), inhibited RTX-induced edema by approximately 96.9%), and a dose of 50 µg/ear of topsentin e, (VI), inhibited RTX-induced edema by approximately 88.4%. In the same model, a dose of 50 µg/ear of dragmacidin f, (II), inhibited RTX-induced edema by approximately 69.9%.

EXAMPLE 4

Formulation and Administration

The compounds of the invention are useful for various non-therapeutic and therapeutic purposes. It is apparent from the testing that the compounds of the invention are effective for anti-inflammatory uses.

Therapeutic application of the new compounds and compositions containing them can be contemplated to be accomplished by any suitable therapeutic method and technique presently or prospectively known to those skilled in the art. Further the compounds of the invention have use as starting material for intermediates for the preparation of other useful compounds and compositions.

In a preferred embodiment, the compounds or compositions of the subject invention are administered in a lotion or other cosmetic preparation. This administration is done directly to the skin where anti-inflammatory activity is desired.

The dosage administration to a host in the above indications will be dependent upon the identity of the infection, the type of host involved, its age, weight, health, kind of concurrent treatment, if any, frequency of treatment and therapeutic ration.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the bis-heterocycle compounds, e.g., a bis-indole, as a first active ingredient plus a second active ingredient comprising an anti-inflammatory compound known in the art. Such known anti-inflammatory drugs include, but are not limited to, the steroidal anti-inflammatory drugs and the non-steroidal anti-inflammatory drugs (NSAIDs).

In accordance with this invention, pharmaceutically effective amounts of a known anti-inflammatory agent and the bis-heterocycle compounds are administered sequentially or concurrently to the patient. The most effective mode of administration and dosage regimen of bis-heterocycle compounds and anti-inflammatory agent will depend upon the type of condition to be treated, the severity and course of that condition, previous therapy, the patient's health status, and response to bis-indoles and the judgment of the treating physician. Bis-heterocycle compositions may be administered to the patient at one time or over a series of treatments.

Preferably, the bis-heterocycle, e.g., a bis-indole composition, and any second anti-inflammatory agent are administered sequentially to the patient, with the anti-inflammatory agent being administered before, after, or both before and after treatment with the bis-indole compound. Sequential administration involves treatment with the anti-inflammatory agent at least on the same day (within 24 hours) of treatment with bis-indole and may involve continued treatment with the anti-inflammatory agent on days that the bis-indole is not administered. Conventional modes of administration and standard dosage regimens of anti-inflammatory agents may be used (see Gilman, A. G. et. al. [eds] *The Pharmacological Basis of Therapeutics,* pp. 697–713, 1482, 1489–1491 [1980]; Physicians Desk Reference, 1985 Edition). For example, indomethacin can be administered orally at a dosage of about 25–50 mg, three times a day. Higher doses can also be used. Alternatively, aspirin (about 1500–2000 mg/day), ibuprofen (about 1200–3200 mg/day), or conventional therapeutic doses of other anti-inflammatory agents can be used. Dosages of anti-inflammatory agents can be titrated to the individual patient.

According to one embodiment of this invention, the patient may receive concurrent treatments with the anti-inflammatory agents and compositions comprising bis-heterocycles, e.g. bis-indoles. For example, local intralesional, or intravenous injection of bis-indoles is preferred (see Gilman et. al. supra at pp. 1290–91). The anti-inflammatory agent should preferably be administered by subcutaneous injection, subcutaneous slow release implant, or orally.

Alternatively, the patient can receive a composition comprising a combination of one or more bis-indole compounds and an anti-inflammatory agent according to conventional modes of administration of agents which exhibit antibacterial, anticancer, antitumor or anti-inflammatory activity. These include, for example, parenteral, subcutaneous, intravenous, or intralesional routes of administration.

The compounds used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch and equivalent carriers and diluents. While effective amounts may vary, as conditions in which compositions are used vary, a minimal dosage required for anti-inflammatory activity is generally between 0.01 and 100 μg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of treating inflammation in a human or animal, wherein said method comprises administering to said human or animal an effective amount of a compound having the following formula:

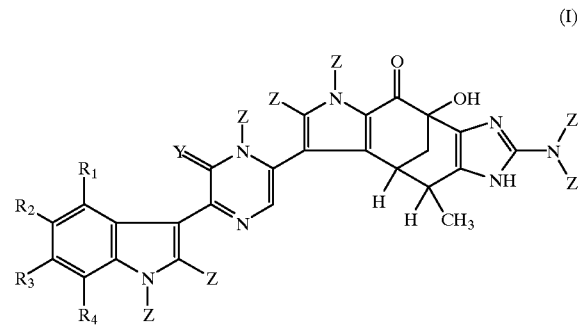

(I)

$R_{1-4}$ are the same or different and are selected from the group consisting of —H, —OH, halogen, —R, —OR, —OCOR, —OA, and NZZ (wherein the Zs can be the same or different);

Y is the single group =O, or the single group =NZ, or two groups, same or different, selected from the group consisting of —H, —OH, —OR, —OCOR, and NZZ (wherein the Zs can be the same or different);

Z is independently selected from the group consisting of —H, —R, —OH, and —COR; and R is C1–C8 alkyl or C1–C8 alkoxyl, mesyl, or tosyl; and A is —R-phenyl.

2. The method, according to claim 1, wherein said compound has the following structure:

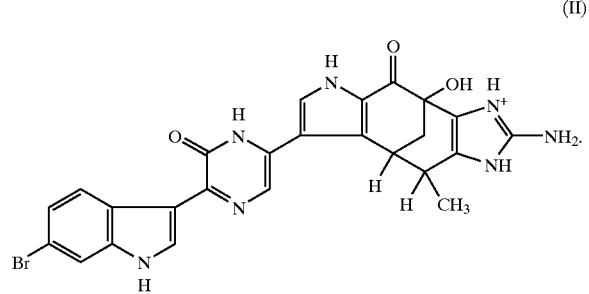

(II)

3. The method, according to claim 1, wherein said method is used to treat inflammation in which the primary activating inflammation is of neurogenic origin.

4. The method, according to claim 3, wherein said method is used to block a nociceptive inflammatory pathway.

5. The method, according to claim 1, wherein said compound is administered as a pharmaceutical composition, said pharmaceutical composition comprising one or more compounds of claim 1 and an acceptable pharmaceutical carrier.

6. The method, according to claim 1, wherein said compound is administered as a cosmetic composition.

7. An anti-inflammatory composition comprising a compound having the formula:

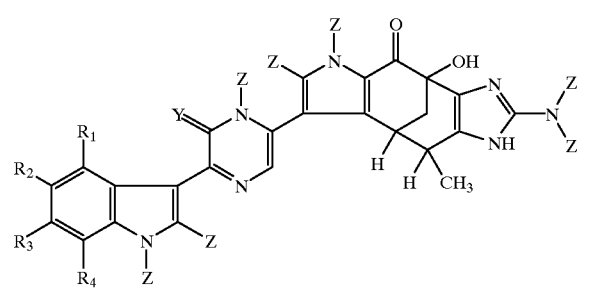

(I)

$R_{1-4}$ are the same or different and are selected from the group consisting of —H, —OH, halogen, —R, —OR, —OCOR, —OA, and NZZ (wherein the Zs can be the same or different);

Y is the single group =O, or the single group =NZ, or two groups, same or different, selected from the group consisting of —H, —OH, —OR, —OCOR, and NZZ (wherein the Zs can be the same or different);

Z is independently selected from the group consisting of —H, —R, —OH, and —COR; and R is C1–C8 alkyl or C1–C8 alkoxyl, mesyl, or tosyl; and A is —R-phenyl.

8. The composition, according to claim 7, wherein said compound has the following structure:

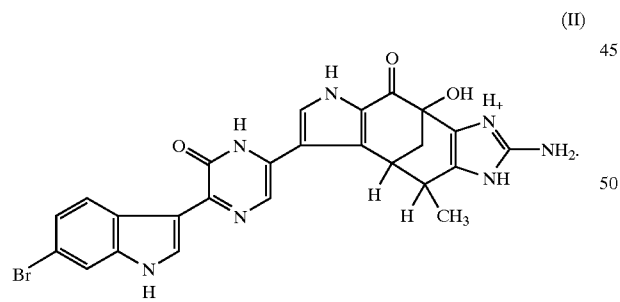

(II)

9. The composition, according to claim 7, wherein said composition further comprises a second active ingredient.

10. The composition, according to claim 9, wherein said second active agent is selected from the group consisting of a steroidal anti-inflammatory compound, a non-steroidal anti-inflammatory compound, an antiviral compound, an antibacterial compound, an antifungal compound, and an anti-tumor compound.

11. The composition, according to claim 7, wherein said compound is about 0.1% to about 45% weight percent of said composition.

12. The composition, according to claim 11, wherein said compound is about 1% to about 25%, weight percent, of said composition.

13. A compound having the following structure:

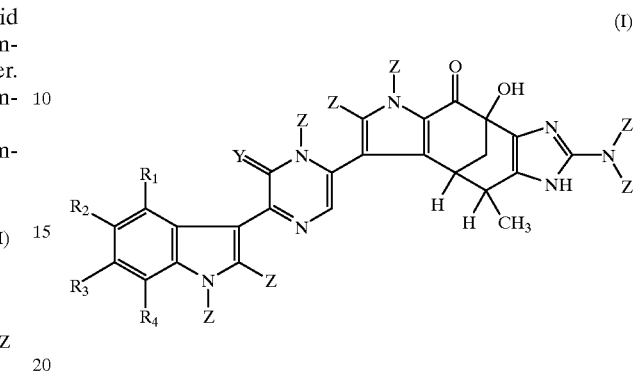

(I)

wherein $R_{1-4}$ are the same or different and selected from the group consisting of —H, —OH, halogen, —R, —OR, —OCOR, —OA, and NZZ (wherein the Zs can be the same or different);

Y is the single group =O, or the single group =NZ, or two groups, same or different, selected from the group consisting of —H, —OH, —OR, —OCOR, and NZZ (wherein the Zs can be the same or different);

Z is independently selected from the group consisting of —H, —R, —OH, and —COR;

R is C1–C8 alkyl or C1–C8 alkoxyl, mesyl, or tosyl; and A is —R-phenyl.

14. The compound, according to claim 13, wherein said compound has the following structure:

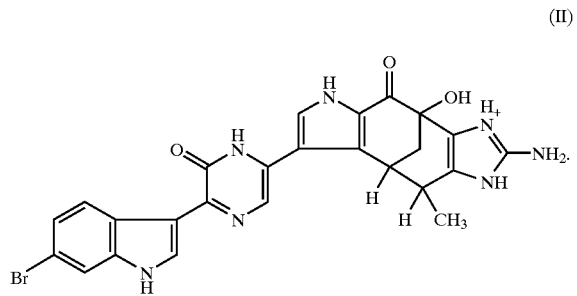

(II)

15. A method for treating a condition, in a human or animal, wherein said condition is selected from the group consisting of pain, burns, allergic responses, wound healing, anaphylactic reactions, inflammatory bowel disease, nephritis, conjunctivitis, inflammatory gum disease, and acute asthmatic attack and inflammation of the lung due to chemical exposure, said method comprising administering an effective amount of a bis-heterocyclic compound or a salt, analog, or derivative thereof, wherein said compound is selected from the group consisting of (I)

R₁₋₄ are the same or different and are selected from the group consisting of —H, —OH, halogen, —R, —OR, —OCOR, —OA, and NZZ (wherein the Zs can be the same or different);

Y is the single group =O, or the single group =NZ, or two groups, same or different, selected from the group consisting of —H, —OH, —OR, —OCOR, and NZZ (wherein the Zs can be the same or different);

Z is independently selected from the group consisting of —H, —R, —OH, and —COR; and R is C1–C8 alkyl or C1–C8 alkoxyl, mesyl, or tosyl; and A is —R-phenyl;

(III)

wherein

R₁₋₈ are the same or different and are selected from the group consisting of —H, —OH, halogen, —R, —OR, —OCOR, —OA, and NZZ (wherein the Zs can be the same or different);

R₉ is selected from the group consisting of $C_{1-8}$ alkyl and aryl;

Z is independently selected from the group consisting of —H, —R, —OH, or —COR;

R is selected from the group consisting of $C_{1-8}$ alkyl or $C_{1-8}$ alkoxyl, mesyl, or tosyl; and A is —R-phenyl; and (V)

wherein

R₁₋₈ are the same or different and are selected from the group consisting of —H, —OH, halogen, —R, —OR, —OCOR, —OA, and NZZ (wherein the Zs can be the same or different);

R₉ is selected from the group consisting of $C_{1-8}$ alkyl and aryl;

Z is independently selected from the group consisting of —H, —R, —OH, or —COR;

R is selected from the group consisting of $C_{1-8}$ alkyl or $C_{1-8}$ alkoxyl, mesyl, and tosyl; and A is —R-phenyl.

16. The method, according to claim 15, wherein said pain is caused by a condition selected from the group consisting of migraine, rhinitis, thermal induced pain, radiation induced pain, and chemical induced pain.

17. The method, according to claim 15, wherein said burn is selected from the group consisting of chemical burns, chemical induced lesions, radiation burns, and thermal burns.

18. The method, according to claim 15, wherein said condition is allergic response.

19. The method, according to claim 15, wherein said treatment facilitates the promotion of wound healing.

20. The method, according to claim 15, wherein said condition is a systemic anaphylactic reaction in an animal or a human.

21. The method, according to claim 15, wherein said condition is inflammatory bowel disease.

22. The method, according to claim 15, wherein said condition is nephritis.

23. The method, according to claim 15, wherein said condition is conjunctivitis.

24. The method, according to claim 15, wherein said condition is inflammatory gum disease.

25. The method, according to claim 15, wherein said condition is selected from the group consisting of acute asthmatic attack and inflammation of the lung from chemical exposure.

* * * * *

UNITED STATES PATENT AND TRADEMARK OFFICE
CERTIFICATE OF CORRECTION

PATENT NO.   : 6,589,957 B2  Page 1 of 1
DATED        : July 8, 2003
INVENTOR(S)  : Amy E. Wright, Shirley A. Pomponi and Robert S. Jacobs It is certified that error appears in the above-identified patent and that said Letters Patent is hereby corrected as shown below:

<u>Column 4,</u>
Line 32, "R is $C_{1-8}$ alkyl or aryl;" should read -- $R_9$ is $C_{1-8}$ alkyl or aryl; --.

<u>Column 5,</u>
Line 23, "R is $C_{1-8}$ alkyl or aryl;" should read -- $R_9$ is $C_{1-8}$ alkyl or aryl; --.

Signed and Sealed this

Twenty-seventh Day of January, 2004

JON W. DUDAS
*Acting Director of the United States Patent and Trademark Office*